(12) United States Patent
Cuca et al.

(10) Patent No.: US 8,057,433 B2
(45) Date of Patent: Nov. 15, 2011

(54) DELIVERY SYSTEM

(75) Inventors: Robert C. Cuca, Glen Carbon, IL (US); Thomas C. Riley, Manchester, MO (US); R. Saul Levinson, Chesterfield, MO (US)

(73) Assignee: DrugTech Corporation, Wilmington, DE (US)

(*) Notice: Subject to any disclaimer, the term of this patent is extended or adjusted under 35 U.S.C. 154(b) by 1228 days.

(21) Appl. No.: 11/571,863

(22) PCT Filed: Jul. 8, 2005

(86) PCT No.: PCT/US2005/024200
§ 371 (c)(1),
(2), (4) Date: Mar. 1, 2007

(87) PCT Pub. No.: WO2006/014572
PCT Pub. Date: Feb. 9, 2006

(65) Prior Publication Data
US 2008/0097388 A1 Apr. 24, 2008

Related U.S. Application Data

(60) Provisional application No. 60/586,273, filed on Jul. 8, 2004.

(51) Int. Cl.
*A61M 1/00* (2006.01)
(52) U.S. Cl. .................................................... 604/118
(58) Field of Classification Search .......... 604/500, 604/891.1, 276–279, 118, 113, 114, 141, 604/142, 246, 251, 253; 424/430, 433, 450; 128/DIG. 12, DIG. 13
See application file for complete search history.

(56) References Cited

U.S. PATENT DOCUMENTS

| | | | |
|---|---|---|---|
| 4,636,202 A | | 1/1987 | Lowin et al. |
| 5,266,329 A | * | 11/1993 | Riley, Jr. .................. 424/430 |
| 5,514,698 A | * | 5/1996 | Ahmad et al. ............. 514/396 |
| 6,364,854 B1 | | 4/2002 | Ferrer et al. |
| 6,403,576 B1 | | 6/2002 | Jackson et al. |
| 6,423,519 B1 | * | 7/2002 | Bergnes et al. ............ 435/193 |
| 6,740,333 B2 | | 5/2004 | Beckett et al. |

FOREIGN PATENT DOCUMENTS

| WO | PCT/US99/27091 A2 | 6/2000 |
|---|---|---|
| WO | 03/079981 A2 | 10/2003 |
| WO | PCT/EP2003/014422 A1 | 7/2004 |
| WO | PCT/EP2006/060190 A1 | 8/2006 |

OTHER PUBLICATIONS

Handbook of Pharmaceutical Excipients, 1986, Propylene Glycol, pp. 241-242, American Pharmaceutical Association, Washington, DC, USA.

* cited by examiner

*Primary Examiner* — Manuel A Mendez
(74) *Attorney, Agent, or Firm* — Senniger Powers LLP

(57) ABSTRACT

A pharmaceutical delivery system that releases an active agent in a controlled manner for an extended period in the vaginal cavity to treat or cure ailments associated with the vaginal cavity or proximal areas. The delivery system includes an applicator which is composed of a high internal phase emulsion, allowing the delivery system to adhere to the mueosal surfaces of the body, primarily the lining of vaginal cavity. The delivery system can maintain the high internal phase emulsion at a temperature of 86° F. for at least one month, without decomposition or instability of the emulsion.

35 Claims, 2 Drawing Sheets

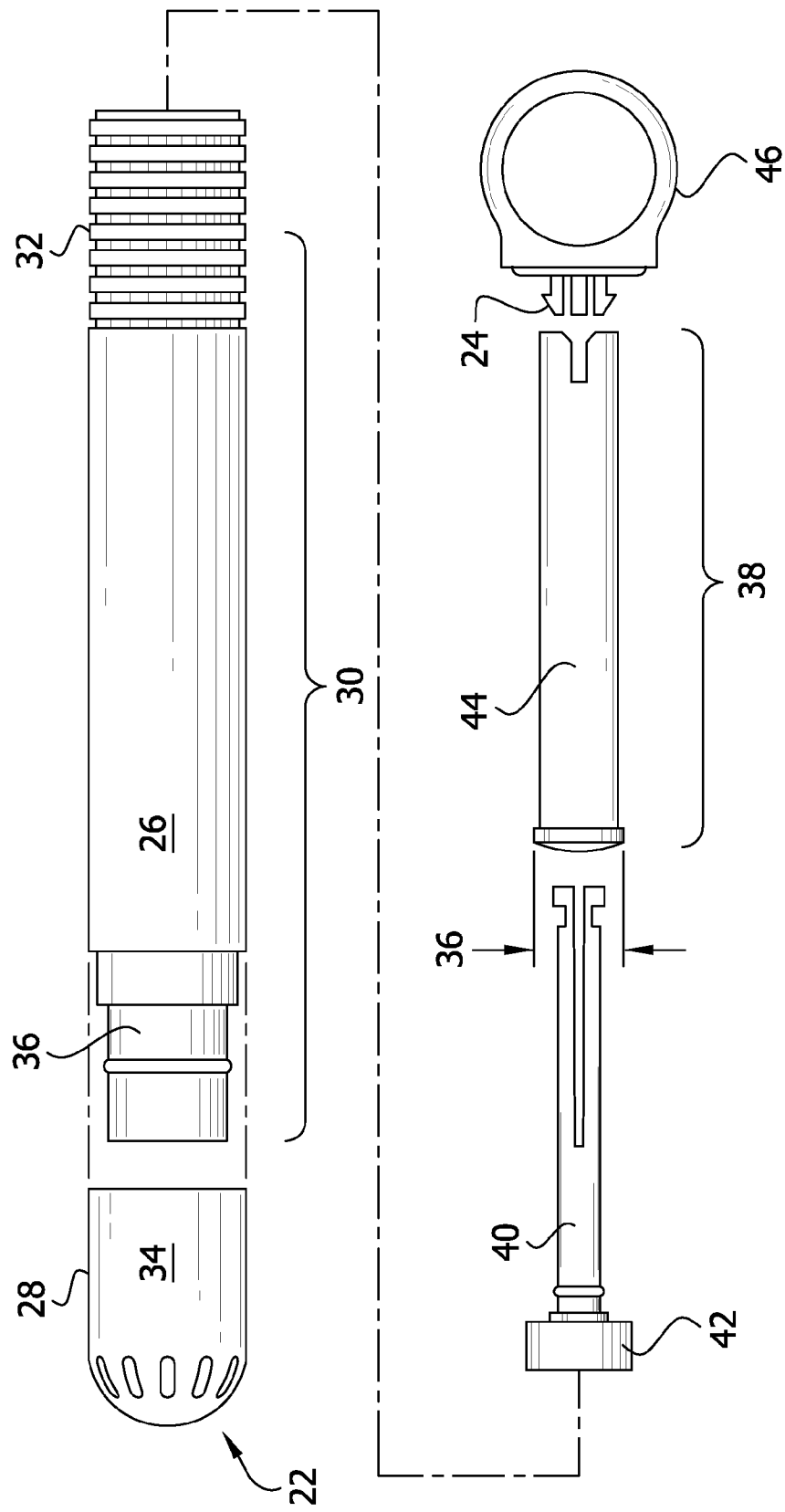

DELIVERY SYSTEM

FIELD OF THE INVENTION

The present invention relates to a pharmaceutical delivery system including an applicator that demonstrates controlled release of active agents, that has a high internal to external phase ratio value, and that is suitable for use in the vaginal cavity.

BACKGROUND OF THE INVENTION

Medical treatment of the female reproductive system for the prevention, control, diagnosis, and cure of disease typically involves the delivery of pharmaceutically active agents to the vaginal cavity and proximal organs. Generally, agents are put in the form of gels, foams, creams, suppositories, and dissolving tablets, or other forms generally known in the art. However, these forms of delivery have not demonstrated the ability to deliver active agents to the vaginal cavity in a controlled manner, particularly for periods of three hours or longer, while providing a high level of bioadherence and a high level of stability in environments having either high or low temperatures.

The biological characteristics of the vagina and proximal areas make it difficult to treat and deliver agents to the vaginal cavity. For example, the vaginal cavity exhibits an aqueous environment, with fluids having a pH in the range of 4.5 to 5.5 and an internal temperature of approximately 98.6° F. (37° C.). The environment of the vaginal cavity is also conducive to the growth of microorganisms, such as bacteria and fungi, including yeast, and the retention of foreign particulates, such as seminal fluid resulting from intercourse, and menstrual debris. The vaginal cavity is also characterized by the ability for considerable physical deformation, such as that resulting from sexual intercourse or insertion of tampons.

Agents, such as fungicides, have typically been used to treat ailments and afflictions in the vaginal cavity. However, the pharmaceutical and chemical activity of these agents has not reached an optimal level of effectiveness. This limitation in effectiveness is due, in part or in whole, to the inadequacy of the currently available delivery systems. In fact, the currently available delivery systems have not shown the ability to release a pharmaceutically active agent in an optimally safe manner for periods of three hours or greater, without encountering problems related to bioadherence or excessive release of the active pharmaceutical ingredient. For instance, delivery systems that are available generally begin to either solubilize, disperse or liquefy almost immediately following insertion into the vaginal cavity. Thus, these delivery systems typically have minimal bioadherence to the vaginal walls.

Conventional delivery systems having a large proportion of propylene glycol in the formulation have been used to enhance the availability of the incorporated drug. The advantage being taken of both the potential solubilization of the active pharmaceutical compound in a solvent like molecule such as propylene glycol and the increased penetration potential afforded by propylene glycol through biological membranes. This extrapolation to delivery systems for mucosal membranes can be overstated, particularly when used in the vaginal cavity. The aqueous nature of the environment provides optimum conditions for systemic absorption of solubilized active pharmaceutical compounds. Inclusion of high concentrations of compounds which solubilize active pharmaceutical agents can increase the systemic absorption potential of that agent. Though in some instances this is a desired effect, in the treatment of local mucosal infections the removal of the beneficial drug from the immediate area can prolong the treatment regime, and in some cases may cause systemic absorption of active pharmaceutical compounds to reach levels that are not beneficial.

In addition there can be physical aspects of the delivery system that are compromised by the inclusion of moderate to excessive amounts of propylene glycol. For conventional emulsions, moderate to excessive amounts propylene glycol can add to the solubilization and liquification of the delivery system in the hydrophilic environment of the vaginal cavity. For more unique emulsion systems the inclusion of higher levels of propylene glycol can lead to physical instability at both ambient and elevated temperatures.

As a result, the emulsions of conventional and unique delivery systems may not provide optimal treatment in the vaginal cavity. There is an unmet need in the art for a controlled release delivery system providing optimal treatment of vaginal ailments and afflictions. Accordingly, there is an unmet need for a delivery system providing a consistent release of a pharmaceutically active agent to the vaginal cavity, specifically a system allowing pharmaceutical activity for an extended period of time, such as at least three hours, and providing high levels of bioadherence. Furthermore, there is an unmet need in the art for a delivery system that reduces the proportion of propylene glycol in the formulation.

SUMMARY OF THE INVENTION

The present invention overcomes the above-mentioned problems, as well as others, by providing a delivery system for the vaginal cavity having increased effectiveness over the delivery systems currently available. In particular, a first embodiment of the present invention provides a delivery system for the treatment of fungal infections of the human female vaginal cavity comprising an effective amount of imidazole derivative active agent and one or more pharmaceutically acceptable excipients which allow the active agent to be released in a controlled manner to a site in the vaginal cavity, wherein the delivery system is an emulsion that exhibits an internal to external phase ratio of greater than 70%. A second embodiment of the present invention is a method of treating a vaginal fungal infection in a female human, comprising administering to the vaginal cavity a delivery system having an effective amount of an imidazole derivative active agent and one or more pharmaceutically acceptable excipients which allow the active agent to be released in a controlled manner to a site in the vaginal cavity, wherein the delivery system is an emulsion that exhibits an internal to external phase ratio of greater than 70%.

More specifically, the delivery system comprises a compact, prefilled, ready-to-use, applicator for dispensing a medicament to a body cavity includes an elongated body having a proximal dispensing end and a distal grasping end. The body is of a sufficient length to dispense medicament to a desired location within a selected body cavity. A proximal portion of the elongated body forms a reservoir adapted to contain a predetermined amount of medicament. A distal portion of the elongated body forms a plunger housing. Closure means are disposed at the dispensing end of the reservoir, and impeller means are disposed at its distal end, at the junction of the reservoir and plunger assembly housing. A telescoping plunger rod assembly, having stop means associated therewith for limiting telescopic extension and preventing telescopic collapse of the plunger rod assembly, is connected to the impeller means. Grasping means are provided for operating said telescoping plunger rod assembly. The applicator is operated by holding it at the grasping end and inserting it, closure end first, into the desired cavity. The plunger assembly is drawn back via the grasping means to the limit of the stop means, and then the plunger assembly is pushed proximally relative to the elongated body, thereby creating pressure to open the closure member and dispense the medicament from the reservoir Other features of the present invention will become apparent connection with the accompanying drawings. Additional advantages and novel features of the invention will also become more apparent to those skilled in the art upon examination of the following or upon learning by practice of the invention.

DESCRIPTION OF THE PREFERRED EMBODIMENTS

In the accompanying sheet of drawing:

FIG. 2 is an exploded view of the medicament applicator of FIG. 1, showing a closure portion, a cylindrical body portion, a first plunger member and second plunger member (together forming a plunger assembly), and a grasping member;

Figure 1:
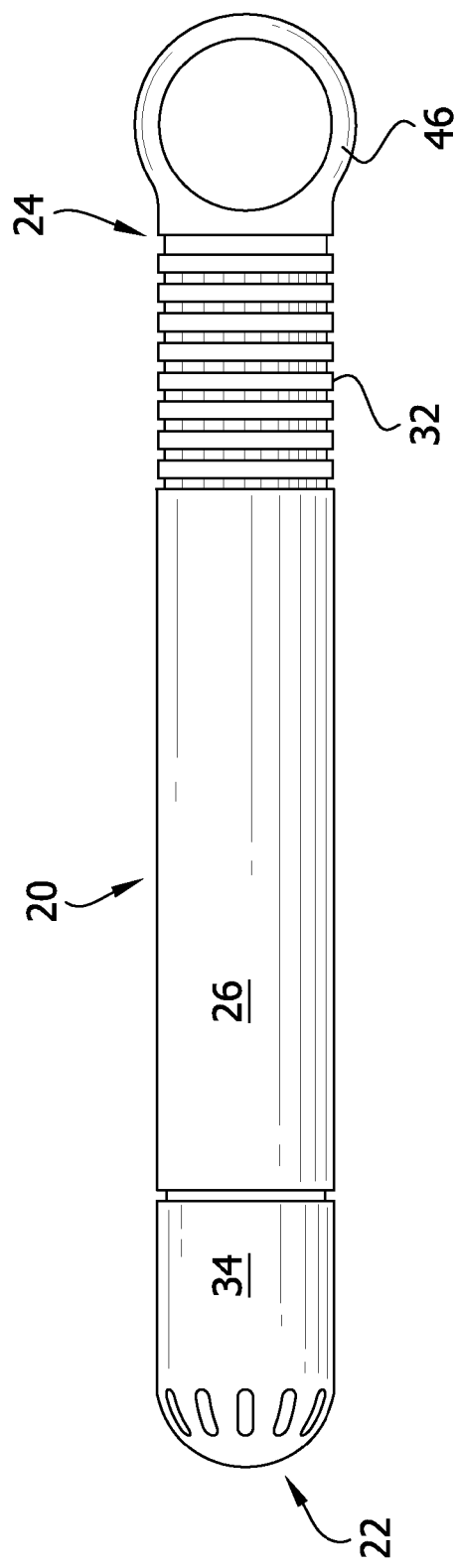
FIG. 1 is a side elevational view of a medicament applicator illustrating the principles of the present invention, shown in the compact, ready-to-use position.

As illustrated in FIGS. 1 and 2 a medicament applicator 20 has a dispensing end 22 and a grasping end 24. A cylindrical member 26 serves as the main body of the applicator, having a medicament reservoir portion, a plunger assembly housing portion, and a grasping surface portion 32. A closure member 34 is slidingly received over a reduced outer diameter portion 36 of the cylindrical member 26. A plunger assembly 38, having a first plunger member 40 with a piston portion 42 and a second plunger member 44, is slidingly received within cylindrical member 26; the piston portion 42 being disposed within the medicament reservoir portion 28 and the rest of the plunger assembly 38 being disposed within the plunger assembly housing portion 30. A grasping member 46 is provided for the second plunger member 44.

The present invention provides a delivery system that provides an emulsion that exhibits a high internal to external phase ratio between 70% to 90%, preferably wherein the nonlipoidal phases comprise from about 70% to 90% by volume of the system. The formulations of the present invention reduce the amount of propylene glycol from commercially available bioadhesive systems, preferably by about 20% to about 80%, more preferably about 25%, compared to the formulations in the prior art, while still maintaining the same high internal emulsion ratio of 70% to 90%.

Additionally, the present invention can sustain a temperature of 86° F. for at least one month, preferably greater than one month, more preferably greater than two months, more preferably greater than six months, and more preferably greater than one year, for example three to five years. The increased stability allows the present invention to be stored in environments susceptible to climate changes or temperature extremes. This improvement is generally known as "improved shelf life."

This invention provides a delivery system for the vaginal cavity, wherein the system delivers pharmaceutically active agents to the vaginal cavity in a controlled manner over an extended period of time. In one variation of the present invention, the extended period of time is at least three hours, and in most cases, the period of time can last as long as ten days or more. The delivery system is characterized by a high internal emulsion ratio. The delivery system is preferably an emulsion comprised of at least 70% hydrophilic constituents by volume of the system.

The delivery system provides agents that restore and maintain a healthy vaginal environment, and cure ailments or afflictions affecting the vaginal cavity. The "vaginal cavity" also includes proximal areas, e.g., it includes the vagina, female urinary tract, such as the ostium of the urethra, organs and tissues at the opening of the vaginal cavity, as well as reproductive organs accessible through the cavity. The delivery system is also characterized by a capability to adhere (otherwise known as "bioadhere") to the walls of the vaginal cavity and proximal areas, including epithelial cells, tissue and organs.

The delivery system not only releases an active agent, but it releases the agent in a controlled manner to obtain optimal absorption. Thus, the active agent is made available for absorption, pharmacological or other effect at a site of absorption or action in an amount sufficient to cause a desired response consistent with the intrinsic properties of the agent and which provides for maintenance of this response at an appropriate level for a desired period of time. The delivery system of the present invention is preferably characterized by the controlled release of the active agent to a receptor site, site of action, site of absorption, or site of use and the achievement of the desired effect at that site. The delivery system is preferably not miscible in water and is not harmful for use in the vaginal cavity.

The delivery system of the present invention can comprise a combination of active and non-active pharmaceutical ingredients (also known generally herein as "excipients"). Non-active ingredients, for example, serve to solubilize, suspend, thicken, dilute, emulsify, stabilize, preserve, protect, color, flavor, and fashion the active ingredients into an applicable and efficacious preparation that is safe, convenient, and otherwise acceptable for use. Active ingredients, which, for example, can constitute 1.0% to 10% of the total weight percent of the delivery system, preferably from about 1.5% to 2.5%, more preferably about 2.0%, provide medicinal or chemical treatment of the vaginal cavity. These active ingredients are formulated to be released in a controlled manner. Active ingredients comprising the active agent may be any of those ingredients that are approved for or are used for the treatment, prophylaxis, cure, or mitigation of any disease of the vaginal cavity. The primary active ingredients of the delivery system of the present invention are imidazole derivatives, which are antifungal and antibacterial in nature. The imidazole derivatives may be present in the form of pharmaceutically acceptable salts, such as nitrates. Examples of imidazole derivatives that can be used in this invention include miconazole nitrate, butoconazole nitrate, oxiconazole nitrate, metronidazole nitrate, terconazole nitrate, and clotrimazole nitrate, among others known in the art. A preferred imidazole derivative in the delivery system of the present invention is butoconazole nitrate.

The delivery system can be comprised of internal phase unit cells. These unit cells are the basic, nondivisable, repeating unit of the systems. The internal phase may be nonlipoidal, i.e., miscible with water, and may comprise water, glycerine, or combinations thereof. The internal phase may be multiphasic and may be a solution, suspension, emulsion, or combination thereof, and may contain at least a portion of the active agent. The external phase may be a continuous phase and lipoidal, i.e., containing organic compounds comprising the neutral fats, fatty acids, waxes, phosphatides, petrolatum, fatty acid esters of monoprotic alcohols and mineral oils that are insoluble in water but soluble in alcohol, ether, chloroform or other fat solvents.

The delivery system may be classified conventionally, for example, as emulsions, emulsions/dispersions, double emulsions, suspensions within emulsions, suppositories, foams, or another classification known in the art. Accordingly, in embodiments of the invention, the delivery systems can vary in form. In one embodiment of the present invention, the system is an emulsification of ingredients in a cream form. Other embodiments of the present invention include lotions, gels, foams, and various emulsifications. The preferred embodiment has a viscosity range from about 5,000 to 2,000,000 centipoise. Additionally, other embodiments of the present invention include liquids, semi-solids and solids having a viscosity range from about 5,000 to 750,000 centipoise, preferably 350,000 to 650,000 centipoise. Optimizing viscosity can allow the system of delivery to achieve maximum bioadherence on the vaginal cavity.

The delivery system is preferably in the form of an emulsion of medium or high internal phase ratio, which is the ratio between the external phase and the internal phase. The ratio value represents how much the internal phase comprises of the system in terms of percent by volume of the system. In embodiments of this invention, the ratio can be at least 70% by volume, preferably at least 75%, more preferably at least 80% and even more preferably up to about 90%.

The controlled release feature of the present invention is a product of the high internal phase emulsion exhibited by the present invention. Emulsifiers, auxiliary agents, emulsifying agents or other excipients, such as glycerol monostearate, glycerol monoisostearate, methylparaben, propylparaben, and generally oils, glycerides, sucrose esters, sorbitan esters, polysorbates, stearoyl lactylates, lecithin and other like compounds, create emulsified globules comprised of non-active ingredients. The globules contain reservoirs of the active agents. These globules slowly disperse upon application, i.e., the globules tend to seek the containing surfaces or membranes, and the globules spread locally (i.e., in the vaginal cavity), thereby forming a "film" containing globules that releases the active agent, in a controlled release fashion, over time. This process occurs over a period of time, such as, for example, three hours to up to ten days or more, and is therefore generally known as "controlled release."

The bioadherence feature of the present invention is a product of the high internal phase emulsion exhibited by the present invention. The emulsified globules, which are comprised of excipients (examples of which are listed above), are small in volume, but have a relatively high surface area. The surface area and nature of the surfaces allows the globules to interact with human tissue through a number of physical binding molecular forces such as Van der Waals forces or hydrogen bonding. These binding forces are intensified due to the high internal phase ratio of the emulsion, there being such a large number of these very small globules as compared to the small volume of the continuous or external phase comprising the emulsion.

The present application incorporates by reference in its entirety U.S. Pat. No. 5,266,329 which issued on Nov. 30, 1999 to Riley, Jr. ("Riley"). At least one change between the delivery system of the present invention and conventional delivery systems, including those disclosed in Riley, is the stability of the delivery system. Propylene glycol can affect the stability and diffusion rate of the delivery system. Propylene glycol can be included in the formulation of the delivery system to serve as a solvent that helps to dissolve the active ingredient of the delivery system, e.g., the imidazole, such as butoconazole nitrate. It has been known in conventional formulations to use propylene glycol at 5.00 weight percent.

In embodiments of the present invention, the propylene glycol can be present in an amount from about 1.0 to about 4.0 weight percent, more preferably from about 3.5 to about 3.85 weight percent, and most preferably about 3.75 weight percent, i.e., the amount of propylene glycol is reduced by about 25% as compared to the 5.00 weight percent believed to be required in prior delivery systems.

An exemplary embodiment for the delivery system of the present invention is as follows:

| Butoconazole Nitrate Cream, 2.0% | |
|---|---|
| Ingredients | Wt % |
| Water Purified, USP | 39.069 |
| Sorbitol Solution, USP | 39.978 |
| Propylene Glycol, USP | 3.75 |
| Edetate Disodium, USP | 0.050 |
| Butoconazole Nitrate, USP | 2.000 |
| Mineral Oil, USP | 8.032 |
| Polyglyceryl-3-Oleate | 2.713 |
| Glyceryl Monisostearate | 2.713 |
| Microcrystalline Wax, NF | 0.452 |
| Silicon Dioxide, Hydrophobic | 1.013 |
| Methylparaben, PF | 0.180 |
| Propylparaben, NF | 0.050 |

The delivery system of at least some embodiments of the present invention improves upon the delivery systems known in the art by reducing the amount of propylene glycol in the formulation. The reduction of propylene glycol does not affect the internal phase emulsion ratio, which is greater than 70%, nor does it preclude the formation of an emulsion. Moreover, the reduction of propylene glycol used achieves unexpected results that are highly advantageous and beneficial to the pharmaceutical and medicinal arts.

The delivery system of the present invention overcomes the limitations of the prior art. For example, reducing the amount of propylene glycol improves the diffusion rate of the active pharmaceutical agent in the delivery system while maintaining its beneficial pharmaceutical properties and effectiveness.

Additionally, the delivery system of embodiments of the present invention has demonstrated physical attributes such as bioadherence and potentially increased physical stability in relation to phase separation and the ability to remain in place resisting dispersion for extended periods of time. The overall increased physical attributes of the delivery system of the present invention provides a more effective product for the consumer and a more optimal treatment in the vaginal cavity, i.e., the emulsion is stable and has improved control over diffusion rates of the active pharmaceutical ingredient thus is more effective. Finally, the increased stability provides increased shelf life in areas where temperatures may be uncontrolled, further allowing the delivery system to be used by a greater number of people.

Exemplary embodiments of the present invention have now been described in accordance with the above advantages. It will be appreciated that these examples are merely illustrative of the invention. Many variations and modifications will be apparent to those skilled in the art.

What is claimed:
1. A delivery system comprising:
an effective amount of an active agent;
propylene glycol; and
one or more pharmaceutically acceptable excipients which allow the active agent to be released in a controlled manner to a site in the vaginal cavity, wherein the delivery system is an emulsion having an internal to external phase ratio of greater than 70% after storage at a temperature of 86° F. for at least one month and wherein the propylene glycol content of the delivery system is about 4.0 weight percent or less.

2. The delivery system according to claim 1, wherein the active agent is an antifungal agent.

3. The delivery system according to claim 2, wherein the antifungal active agent constitutes about 1.5% to 3% of the total weight percent of the delivery system.

4. The delivery system according to claim 2, wherein the antifungal active agent is an imidazole derivative.

5. The delivery system according to claim 4, wherein the delivery system is comprised of at least 80% hydrophilic constituents by volume of the delivery system.

6. The delivery system according to claim 4, wherein the imidazole derivative is selected from a group consisting of miconazole, butoconazole, oxiconazole, metronidazole, and clotrimazole, or a pharmaceutically acceptable salt thereof.

7. The delivery system according to claim 6, wherein the imidazole derivative is butoconazole, or the pharmaceutically acceptable salt thereof.

8. The delivery system according to claim 4, wherein the imidazole derivative active agent is present in a range from about 1.5% to about 3% of the total weight percent of the delivery system, and further comprising:
propylene glycol in a range from about 1.0% to about 4.0% of the total weight percent of the delivery system.

9. The delivery system according to claim 1, wherein the delivery system is comprised of at least 70% hydrophilic constituents by volume of the delivery system.

10. The delivery system according to claim 9, wherein the delivery system is comprised of up to about 90% hydrophilic constituents by volume of the delivery system.

11. The delivery system according to claim 1, wherein the system exhibits bioadhesion to the vaginal cavity walls.

12. The delivery system according to claim 1, wherein the delivery system is in a form selected from the group consisting of an emulsion, emulsion/dispersion, double emulsion, and a suspension within an emulsion or mixture.

13. The delivery system according to claim 1, wherein the delivery system contains about 3.75 weight percent or less propylene glycol.

14. The delivery system according to claim 1, wherein the delivery system contains propylene glycol in a range from about 1.0 weight percent to about 4.0 weight percent.

15. The delivery system according to claim 1, wherein the delivery system has an internal phase emulsion ratio of greater than 70% after storage at a temperature of 86° F. for greater than one month.

16. The delivery system according to claim 1, wherein the delivery system has an internal phase emulsion ratio of greater than 70% after storage at a temperature of 86° F. for at least two months.

17. The delivery system according to claim 1, wherein the delivery system has an internal phase emulsion ratio of greater than 70% after storage at a temperature of 86° F. for at least six months.

18. The delivery system according to claim 1, wherein the delivery system has an internal phase emulsion ratio of greater than 70% after storage at a temperature of 86° F. for at least one year.

19. The delivery system according to claim 1, wherein the delivery system allows for controlled release of the active agent to the site in the vaginal cavity for at least three hours.

20. The delivery system according to claim 1, wherein the delivery system is in a form of a liquid or a semi-solid having a viscosity of from about 5,000 to about 2,000,000 centipoise.

21. The delivery system according to claim 20, wherein the delivery system is in a form of a liquid or a semi-solid having a viscosity of from about 5,000 to about 750,000 centipoise.

22. The delivery system according to claim 21, wherein the delivery system is in a form of a liquid or a semi-solid having a viscosity of from about 350,000 to about 650,000 centipoise.

23. The delivery system according to claim 1, the active ingredient is present in a range from about 1% to about 10% of the total weight percent of the delivery system.

24. The delivery system according to claim 1, wherein the internal phase is nonlipoidal and the external phase is lipoidal.

25. A delivery system suitable for treating of fungal infections of a human female vaginal cavity comprising:
about 30.0 to about 50.0 weight percent water;
about 30 to about 50 weight percent sorbitol solution;
about 3.0 to about 4.0 weight percent propylene glycol;
about 0.2 to about 0.08 weight percent edetate disodium;
about 1.5 to about 2.5 weight percent butoconazole, or the pharmaceutically acceptable salt thereof;
about 7.0 to about 9.0 weight percent mineral oil;
about 2.0 to about 3.5 weight percent polyglyceryl-3-oleate;
about 2.0 to about 3.5 weight percent glyceryl monisostearate;
about 0.2 to about 0.80 weight percent microcrystalline wax;
about 0.5 to 1.5 weight percent hydrophobic silicon dioxide;
about 0.1 to about 0.3 weight percent methylparaben; and
about 0.02 to about 0.08 weight percent propylparaben.

26. The delivery system according to claim 25, wherein the delivery system comprises:
about 37.819 weight percent water;
about 39.978 weight percent sorbitol solution;
about 3.750 weight percent propylene glycol;
about 0.050 weight percent edetate disodium;
about 2.000 weight percent butoconazole or the pharmaceutically acceptable salt thereof;
about 8.032 weight percent mineral oil;
about 2.713 weight percent polyglyceryl-3-oleate;
about 2.713 weight percent glyceryl monisostearate;
about 0.452 weight percent microcrystalline wax;
about 1.013 weight percent hydrophobic silicon dioxide;
about 0.180 weight percent methylparaben; and
about 0.050 weight percent propylparaben.

27. A delivery system suitable for treating of fungal infections of the human female vaginal cavity consisting essentially of:
about 35 to about 45 weight percent water;
about 35 to about 45 weight percent sorbitol solution;
about 3.0 to about 4.0 weight percent propylene glycol;
about 0.02 to about 0.08 weight percent edetate disodium;
about 1.5 to about 2.5 weight percent butoconazole or the pharmaceutically acceptable salt thereof;
about 7.0 to about 9.0 weight percent mineral oil;
about 2.0 to about 3.5 weight percent polyglyceryl-3-oleate;
about 2.0 to about 3.5 weight percent glyceryl monisostearate;
about 0.02 to about 0.08 weight percent microcrystalline wax;

about 0.5 to 1.5 weight percent hydrophobic silicon dioxide;
about 0.1 to about 0.3 weight percent methylparaben; and
about 0.02 to about 0.08 weight percent propylparaben.

28. A method of treating a vaginal fungal infection in a female human, comprising:
administering to the vaginal cavity a delivery system having an effective amount of an imidazole derivative active agent propylene glycol and one or more pharmaceutically acceptable excipients which allow the active agent to be released in a controlled manner to a site in the vaginal cavity, wherein the delivery system is an emulsion having an internal to external phase emulsion ratio of greater than 70% after storage at a temperature of 86° F. for at least one month and wherein the propylene glycol content of the delivery system is about 4.0 weight percent or less.

29. The method according to claim 28, wherein the active agent is released for at least three hours.

30. The method according to claim 28, wherein the imidazole derivative active agent is butoconazole or the pharmaceutically acceptable salt thereof.

31. The method according to claim 28, wherein the effective amount of the imidazole derivative active agent constitutes about 1.5% to about 3% of the total weight percent of the delivery system.

32. The method according to claim 28, wherein the imidazole derivative active agent is present in an amount ranging from about 1.5% to about 3% the total weight percent of the delivery system and propylene glycol is present in an amount ranging from about 1.0% to about 4.0% of the total weight percent of the delivery system.

33. A delivery system which comprises an applicator comprising: a compact, prefilled, ready-to-use, applicator for dispensing a medicament to the vaginal cavity, said applicator having an elongated body having a proximal dispensing end and a distal grasping end;
said body is of a sufficient length to dispense medicament to a desired location within the vaginal cavity;
a proximal portion of the elongated body forms a reservoir adapted to contain a predetermined amount of medicament;
a distal portion of the elongated body forms a plunger housing; closure means are disposed at the dispensing end of the reservoir, and impeller means are disposed at its distal end, at the junction of the reservoir and plunger assembly housing;
a telescoping plunger rod assembly having stop means associated therewith for limiting telescopic extension and preventing telescopic collapse of the plunger rod assembly connected to the impeller means;
and grasping means for operating said telescoping plunger rod assembly;
said medicament having an effective amount of an active agent propylene glycol and one or more pharmaceutically acceptable excipients which allow the active agent to be released in a controlled manner to a site in the vaginal cavity, wherein the delivery system is an emulsion having an internal to external phase emulsion ratio of greater than 70% after storage at a temperature of 86° F. for at least one month and wherein the propylene glycol content of the delivery system is about 4.0 weight percent or less.

34. The delivery system according to claim 33, wherein the active agent is an antifungal.

35. An applicator containing a delivery system comprising:
an effective amount of an active agent;
propylene glycol; and
one or more pharmaceutically acceptable excipients which allow the active agent to be released in a controlled manner to a site in the vaginal cavity,
wherein the delivery system is an emulsion having an internal to external phase emulsion ratio of greater than 70% after storage at a temperature of 86° F. for at least one month and
wherein the propylene glycol content of the delivery system is about 4.0 weight percent or less.

* * * * *